(12) United States Patent
Abelson et al.

(10) Patent No.: US 12,048,685 B2
(45) Date of Patent: Jul. 30, 2024

(54) TRANSIENT RECEPTOR POTENTIAL CATION CHANNEL SUBFAMILY M MEMBER 8 (TRPM8) ANTAGONISTS AND METHODS OF USE

(71) Applicant: Ora, Inc., Andover, MA (US)

(72) Inventors: Mark B. Abelson, Teton Village, WY (US); Peter Corcoran, Somerville, MA (US); Keith Lane, Stow, MA (US)

(73) Assignee: Ora, Inc., Andover, MA (US)

(*) Notice: Subject to any disclaimer, the term of this patent is extended or adjusted under 35 U.S.C. 154(b) by 0 days.

(21) Appl. No.: 16/802,055

(22) Filed: Feb. 26, 2020

(65) Prior Publication Data

US 2020/0188355 A1    Jun. 18, 2020

Related U.S. Application Data

(60) Division of application No. 15/417,850, filed on Jan. 27, 2017, now Pat. No. 10,603,303, which is a continuation of application No. PCT/US2016/055677, filed on Oct. 6, 2016.

(60) Provisional application No. 62/237,672, filed on Oct. 6, 2015.

(51) Int. Cl.
*A61K 31/381* (2006.01)
*A61K 9/00* (2006.01)
*A61K 45/06* (2006.01)

(52) U.S. Cl.
CPC .......... *A61K 31/381* (2013.01); *A61K 9/0048* (2013.01); *A61K 45/06* (2013.01)

(58) Field of Classification Search
CPC .................................................. A61K 31/381
See application file for complete search history.

(56) References Cited

U.S. PATENT DOCUMENTS

| | | | |
|---|---|---|---|
| 9,125,807 B2 | 9/2015 | Sawhney et al. | |
| 10,603,303 B2 | 3/2020 | Abelson et al. | |
| 2008/0214654 A1 | 9/2008 | Lampe et al. | |
| 2009/0131449 A1 | 5/2009 | Yanni et al. | |
| 2013/0245231 A1* | 9/2013 | Belmonte Martinez | A61K 31/4164 |
| | | | 530/387.3 |

FOREIGN PATENT DOCUMENTS

| | | |
|---|---|---|
| WO | WO 2006/040136 A1 | 4/2006 |
| WO | WO 2007/017092 A1 | 2/2007 |
| WO | WO 2007/017094 A1 | 2/2007 |
| WO | WO 2007/017093 A1 | 5/2007 |
| WO | WO 2007/134107 A2 | 11/2007 |
| WO | WO 2009/012430 A1 | 1/2009 |
| WO | WO 2010/103381 A1 | 9/2010 |
| WO | WO 2010/125831 A1 | 11/2010 |
| WO | WO 2017/062570 A1 | 4/2017 |

OTHER PUBLICATIONS

Quallo et al. (Nature Communications (May 2015) pp. 1-12) (Year: 2015).*
Almeida et al. (The Journal of Neuroscience (2012) 32:2086-2099). (Year: 2012).*
Abe, J. et al., "Ca2+-dependent PKC activation mediates menthol-induced desensitization of transient receptor potential M8," Neuroscience Letters, 397:140-144 (2006).
Abeele, F. V. et al., "Ca2+ -independent Phospholipase A2-dependent Gating of TRPM8 by Lysophospholipids," The Journal of Biological Chemistry, 281(52):40174-40182 (2006).
Abelson, M. B. et al., "Dry eye in 2008," Curr Opin Ophthalmol, 20:282-286 (2009).
Acosta, M. C. et al., "Sensations Evoked by Selective Mechanical, Chemical, and Thermal Stimulation of the Conjunctiva and Cornea," Invest Ophthalmol Vis Sci., 42:2063-2067 (2001).
Acosta, M. C. et al., "Sensory experiences in humans and single-unit activity in cats evoked by polymodal stimulation of the cornea," Journal of Physiology, 534(2):511-525 (2001).
Acosta, M. C. et al., "Tear Secretion Induced by Selective Stimulation of Corneal and Conjunctival Sensory Nerve Fibers," Invest Ophthalmol Vis Sci., 45(7):2333-2336 (2004).
Barabino, S. & Dana, M. R., "Dry Eye Syndromes," Chem Immunol Allergy, 92:176-184 (2007).
Behrendt, H.-J. et al., "Characterization of the mouse cold-menthol receptor TRPM8 and vanilloid receptor type-1 VR1 using a fluorometric imaging plate reader (FLIPR) assay," British Journal of Pharmacology, 141:737-745 (2004).
Belmonte, C. & Giraldez, F., "Responses of cat corneal sensory receptors to mechanical and thermal stimulation," J. Physiol., 321:355-368 (1981).
Cannon, J. G., Chapter 19 in Burger's Medicinal Chemistry and Drug Discovery, Fifth Edition, vol. 1: Principles and Practice, Wiley-Interscience, 1996, pp. 783-802 (1995).
CAS Registry No. 926023-82-7, Mar. 12, 2007, 1 page.
CAS No. Registry 1259026-14-6, Jan. 12, 2011, 2 pages.
Chen, W. et al., "A Murine Model of Dry Eye Induced by an Intelligently Controlled Environmental System," Investigative Ophthalmology & Visual Science, 49(4): 1386-1391 (2008).
Chen, Z. et al., "Establishment of a Rabbit Model for Keratoconjunctivitis Sicca," Cornea, 30:1024-1029 (2011).
Chen, G.- L. et al., "Borneol Is a TRPM8 Agonist that Increases Ocular Surface Wetness," PLoS One, 11(7):e0158868 (2016), 15 pages; doi:10.1371/journal.pone.0158868.

(Continued)

*Primary Examiner* — Marcos L Sznaidman
(74) *Attorney, Agent, or Firm* — COOLEY LLP; Ivor R. Elrifi; Cynthia A. Kozakiewicz

(57) ABSTRACT

The invention provides methods of treating or preventing an ocular disease or disorder in a subject, methods of treating or preventing ocular pain or discomfort comprising, administering to the subject a composition comprising a pharmaceutically acceptable carrier and a pharmaceutically effective amount of a transient receptor potential melastatin 8 (TRPM8) antagonist. In certain preferred embodiments, the ocular disease or disorder is a dry eye disease.

6 Claims, 11 Drawing Sheets

(56) References Cited

OTHER PUBLICATIONS

Dartt, D. A., "Dysfunctional Neural Regulation of Lacrimal Gland Secretion and its Role in the Pathogenesis of Dry Eye Syndromes," The Ocular Surface, 2(2):76-91 (2004).
Dartt, D. A., "Neural regulation of lacrimal gland secretory processes: Relevance in dry eye diseases," Progress in Retinal and Eye Research, 28:155-177 (2009).
De Almeida, D. E. et al., "Conjunctival effects of canine distemper virus-induced keratoconjunctivitis sicca," Veterinary Ophthalmology, 12(4):211-215 (2009).
De Petrocellis, L. et al., "Regulation of transient receptor potential channels of melastatin type 8 (TRPM8): Effect of cAMP, cannabinoid CB1 receptors and endovanilloids," Experimental Cell Research, 313:1911-1920 (2007).
François, J. et al., "Experimental Keratitis Sicca. The Corneal Epithelium at the Transmission and Scanning Electron Microscope," Ophthalmic Res, 8:414-424 (1976).
Fujihara, T. et al., "Establishment of a Rabbit Short-Term Dry Eye Model," Journal of Ocular Pharmacology and Therapeutics, 11(4):503-508 (1995), and Citations, 3 pages.
Fujihara, T. et al., "Improvement of Corneal Barrier Function by the P2Y2 Agonist INS365 in a Rat Dry Eye Model," Investigative Ophthalmology & Visual Science, 42(1):96-100 (2001).
Gilbard, J. P. et al., "A New Rabbit Model For Kerotoconjunctivitis Sicco," Invest Ophthalmol Vis Sci, 28:225-228 (1987).
Gilbard, J. P. et al., "Tear Film and Ocular Surface Changes after Closure of the Meibomian Gland Orifices in the Rabbit," Ophthalmology, 96:1180-1186 (1989).
Gilbard, J. P. et al., "Natural history of disease in a rabbit model for keratoconjunctivitis sicca," Acta Ophthalmol Supplementum 192:95-101 (1989).
Guo, Z. et al., "Autologous Lacrimal+Lymphoid Mixed-cell Reactions Induce Dacryoadenitis in Rabbits," Exp. Eye Res., 71:23-31 (2000).
Hicks, S. J. et al., "Biochemical Analysis of Ocular Surface Mucin Abnormalities in Dry Eye: The Canine Model," Exp. Eye Res., 67:709-718 (1998).
Hirata, H. & Meng, D., "Cold-Sensitive Corneal Afferents Respond to a Variety of Ocular Stimuli Central to Tear Production: Implications for Dry Eye Disease," Investigative Ophthalmology & Visual Science, 51(8):3969-3976 (2010).
Jain, P. et al., "An NGF mimetic, MIM-D3, stimulates conjunctival cell glycoconjugate secretion and demonstrates therapeutic efficacy in a rat model of dry eye," Experimental Eye Research, 93:503-512 (2011).
Jiang, G. et al., "A New Model of Experimental Autoimmune Keratoconjunctivitis Sicca (KCS) Induced in Lewis Rat by the Autoantigen Klk1b22," Investigative Ophthalmology & Visual Science, 50(5):2245-2254 (2009).
Kaminer, J. et al., "Characterizing the Spontaneous Blink Generator: An Animal Model," The Journal of Neuroscience, 31(31):11256-11267 (2011).
Latkany, R. et al., "Tear Film Normalization Test A New Diagnostic Test for Dry Eyes," Cornea, 25:1153-1157 (2006).
Lavoie, T. N. et al., "Current Concepts: Mouse Models of Sjögren's Syndrome," Journal of Biomedicine and Biotechnology, vol. 2011, Article ID 549107, 2011, 14 pages; doi:10.1155/2011/549107.
Mathers, W. D., "Why the Eye Becomes Dry: A Cornea and Lacrimal Gland Feedback Model," The CLAO Journal, 26(3):159-165 (2000).
Meng, I. D. & Kurose, M., "The role of corneal afferent neurons in regulating tears under normal and dry eye conditions," Experimental Eye Research, 117:79-87 (2013).

McKemy, D. et al., "Identification of a cold receptor reveals a general role for TRP channels in thermosensation," Nature, 416:52-58 (2002).
Nilius, B. et al., "Gating of TRP channels: a voltage connection?," J Physiol, 567(Pt 1):35-44 (2005).
Ogawa, Y. & Tsubota, K., "Dry eye disease and inflammation," Inflammation and Regeneration, 33(5):238-248 (2013).
Parks, D. J. et al., "Design and Optimization of Benzimidazole-Containing Transient Receptor Potential Melastatin 8 (TRPM8) Antagonists," J. Med. Chem., 54:233-247 (2011).
Parra, A. et al., "Ocular surface wetness is regulated by TRPM8-dependent cold thermoreceptors of the cornea," Nature Medicine, 16(12):1396-1399 (2010).
Peier, A. M. et al., "A TRP Channel that Senses Cold Stimuli and Menthol," Cell, 108:705-715 (2002).
Premkumar, L. S. et al., "Downregulation of Transient Receptor Potential Melastatin 8 by Protein Kinase C-Mediated Dephosphorylation," The Journal of Neuroscience, 25(49):11322-11329 (2005).
Rahman, M. et al., "Sensitization of trigeminal brainstem pathways in a model for tear deficient dry eye," Pain, 156:942-950 (2015).
Robbins, A. et al., "Menthol Activation of Corneal Cool Cell Induces TRPM8-Mediated Lacrimation but Not Nociceptive Response in Rodents," IOVS, 53(11): 7034-7042 (2012).
Rohács, T. et al., "PI(4,5)P2 regulates the activation and desensitization of TRPM8 channels through the TRP domain," Nature Neuroscience, 8(5):626-634 (2005).
Schenke-Layland, K. et al., "Lymphocytic infiltration leads to degradation of lacrimal gland extracellular matrix structures in NOD mice exhibiting a Sjögren's syndrome-like exocrinopathy," Experimental Eye Research, 90:223-237 (2010).
Schrader, S. et al., "Animal Models of Dry Eye," Geerling G, Brewitt H (eds): Surgery for the Dry Eye. Dev Ophthalmol. Basel, Karger, 41:298-312 (2008); doi:10.1159/000131097.
Suwan-Apichon, O. et al., "Botulinum Toxin B-Induced Mouse Model of Keratoconjunctivitis Sicca," Investigative Ophthalmology & Visual Science, 47(1):133-139 (2006).
Toshida, H. et al., "Evaluation of Novel Dry Eye Model: Preganglionic Parasympathetic Denervation in Rabbit," Investigative Ophthalmology & Visual Science, 48(10):4468-4475 (2007).
Treede, R.-D. et al., Neuropathic pain. Redefinition and a grading system for clinical and research purposes, Neurology, 70:1630-1635 (2008).
Van Bijsterveld, O. P. et al., "Central nervous system mechanisms in Sjogren's syndrome," Br J Ophthalmol, 87:128-131 (2003).
Xie, H. et al., Abstract: "Ultrastructural Changes of the Corneal Epithelium of the Experimental Dry Rabbit Eye Model and Effects of Several Topical Eye-Drops," Chinese Ophthal. Res. 1992, 10(1), 4 pages.
Xiong, G. et al., "A Rabbit Dry Eye Model Induced by Topical Medication of a Preservative Benzalkonium Chloride," Investigative Ophthalmology & Visual Science, 49(5):1850-1856 (2008).
Yang, J. M. et al., "A novel TRPM8 agonist relieves dry eye discomfort," BMC Ophthalmology, 17:101 (2017), 15 pages; doi. 10.1186/s12886-017-0495-2.
Hirata, H. & Oshinsky, M. L., "Ocular dryness excites two classes of corneal afferent neurons implicated in basal tearing in rats: involvement of transient receptor potential channels," J Neurophysiol, 107(4):1199-1209 (2011).
Almaraz, L. et al., "TRPM8," Handbook of Experimental Pharmacology, Nilius and V. Flockerzi (Eds.), Mammalian Transient Receptor Potential (TRP) Cation Channels vol. I; Springer Verlag, Berlin, DE, Jan. 1, 2014, pp. 547-579.
Evinger, C. et al., "Dry Eye, Blinking, and Blepharospasm," Mov Disord., 17(Suppl 2):S75-S78 (2002).
Messmer, E. M., "The Pathophysiology, Diagnosis, and Treatment of Dry Eye Disease," Dtsch Arztebl Int, 112: 71-82 (2015); doi:10.3238/arztebl.2015.0071.

\* cited by examiner

TRANSIENT RECEPTOR POTENTIAL CATION CHANNEL SUBFAMILY M MEMBER 8 (TRPM8) ANTAGONISTS AND METHODS OF USE

RELATED APPLICATIONS

This application is a divisional of U.S. application Ser. No. 15/417,850, filed on Jan. 27, 2017, which is a continuation of International Application No. PCT/US2016/055677, filed on Oct. 6, 2016, which claims the benefit of priority to U.S. Provisional Application No. 62/237,672, filed on Oct. 6, 2015, the entire contents of which are incorporated by reference in their entireties herein.

BACKGROUND

Tears provide nourishment to the anterior eye and are necessary for its protection from potentially damaging stimuli (Dartt et al., Prog Retin Eye Res 28: 155-177, 2009). Corneal primary afferent neurons involved in noxious stimulus-evoked tearing include both polymodal and mechanoreceptive neurons, and increased tearing caused by activation of these afferents is accompanied by irritation or pain (Acosta et al., J Physiol 534: 511-525, 2001; Acosta et al., Invest Ophthalmol Vis Sci 42: 2063-2067, 2001; Acosta et al., Invest Ophthalmol Vis Sci 45: 2333-2336, 2004). In addition to polymodal and mechanoreceptive afferents, the cornea is innervated by neurons that are sensitive to innocuous cooling (Belmonte and Giraldez J Physiol 321: 355-368, 1981; Hirata and Meng Invest Ophthalmol Vis Sci 51: 3969-3976, 2010). These corneal cool cells are also activated by menthol, an agonist to the transient receptor potential melastatin 8 (TRPM8) channel, and by hyperosmotic stimuli (Acosta et al. 2001; Hirata and Meng 2010). Corneal cool cells are involved in a reflex that promotes tear production in response to drying of the ocular surface (Parra et al., Nat Med 16: 1396-1399, 2010).

Dry eye disease is a relatively common condition characterized by inadequate tear film protection of the cornea. Dry eye symptoms have traditionally been managed with eyelid hygiene, topical antibiotics (erythromycin or bacitracin ointments), oral tetracyclines (tetracycline, doxycycline, or minocycline), anti-inflammatory compounds (cyclosporine) and corticosteroids which are often time consuming, frustrating, and frequently ineffective or variably effective treatments. Tens of millions of people are affected worldwide by dry eye, and nearly five million Americans 50 years of age and older are estimated to have dry eye. Of these, more than three million are women and more than one and a half million are men. Elderly people frequently experience dryness of the eyes, but dry eye can occur at any age. Dry eye is a potentially disabling disease adversely impacting the vision-related quality of life. Current therapeutic options are limited and costly. Despite the high incidence of dry eye disease, it still remains a therapeutic challenge.

Accordingly, there remains a need for new therapies to treat dry eye disease.

SUMMARY OF THE INVENTION

The present invention is based on the novel and surprising finding that a transient receptor potential melastatin 8 (TRPM8) antagonist can be used to treat or prevent an ocular disease or disorder or ocular pain or discomfort in a subject.

In a first aspect, the invention features a method of treating or preventing an ocular disease or disorder in a subject comprising administering to the subject a composition comprising a pharmaceutically acceptable carrier and a pharmaceutically effective amount of a transient receptor potential melastatin 8 (TRPM8) antagonist.

In one embodiment, treating or preventing the ocular disease or disorder comprises treating or preventing the symptoms of the ocular disease or disorder.

In one embodiment, the ocular disease or disorder is ocular discomfort.

In one embodiment, the ocular disease or disorder is a dry eye disease or dry eye discomfort. In a related embodiment, the dry eye disease is severe dry eye disease. In a further related embodiment, the ocular disease or disorder, for example a dry eye disease, is attributable to one or more causes selected from aging, contact lens usage, environmental stress, fatigue, diet, hydration, systemic disease, visual tasking such as reading or video screen use, inflammation or medication usage. In another further embodiment, the ocular disease or disorder, for example a dry eye disease, is due to excessively fast tear evaporation (evaporative dry eyes) or inadequate tear production. In still another further embodiment, the ocular disease or disorder, for example a dry eye disease, is associated with refractive surgery.

In another aspect, the present invention features a method of treating or preventing ocular pain or discomfort in a subject comprising administering to the subject a composition comprising a pharmaceutically acceptable carrier and a pharmaceutically effective amount of a transient receptor potential melastatin 8 (TRPM8) antagonist.

In one embodiment, the ocular pain or discomfort is caused by a dry eye disease. In a further embodiment, the dry eye disease is severe dry eye disease. In a further related embodiment, the dry eye disease is attributable to one or more causes selected from aging, contact lens usage, environmental fatigue, diet, hydration, systemic disease, inflammation or medication usage. In another further embodiment, the dry eye disease is due to excessively fast tear evaporation (evaporative dry eyes) or inadequate tear production. In still another further embodiment, the dry eye disease is associated with refractive surgery.

In another aspect, the present invention features a method of normalizing the tear film in a subject comprising administering to the subject a composition comprising a pharmaceutically acceptable carrier and a pharmaceutically effective amount of a transient receptor potential melastatin 8 (TRPM8) antagonist. Normalizing the tear film is meant to include normalizing the ocular surface.

In one embodiment of any one of the above aspects, the composition is administered topically to the eye, for example administered to the eye or around the eye. In a further embodiment, the eye comprises a tissue or gland in or around the eye selected from the group consisting of ocular tissue, eyelids of the subject, ocular surface, meibomian gland and or lacrimal gland of the human.

In another embodiment of any one of the above aspects, the composition is in the form of a solid, a paste, an ointment, a gel, a liquid, an aerosol, a mist, a polymer, a film, an emulsion, or a suspension.

In another embodiment of any one of the above aspects, the TRPM8 antagonist is selected from the group consisting of a small molecule, a nucleic acid molecule, an aptamer, an antisense molecule, an RNAi molecule, a protein, a peptide and an antibody or antibody fragment. In a further embodiment, the TRPM8 antagonist is a small molecule. In another further embodiment, the TRPM8 small molecule antagonist comprises Compound I:

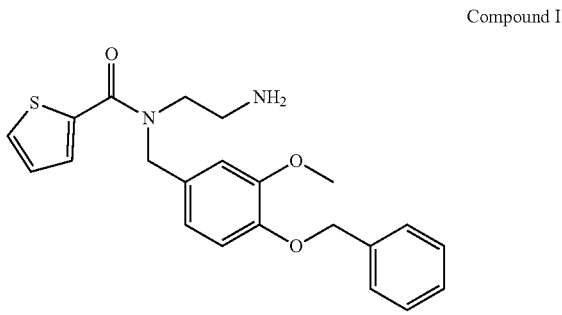 [SMILES: COc1cc(CN(CCN)C(=O)c2cccs2)ccc1OCc1ccccc1]

Compound I

In another embodiment of any one of the above aspects, the pharmaceutically effective amount of the TRPM8 antagonist is 0.001-5.0% (w/v), for example 0.001-5.0% (w/v), 0.01-5.0% (w/v), 0.1-5.0% (w/v), 1.0-5.0% (w/v). In a related embodiment, the pharmaceutically effective amount of the TRPM8 antagonist is 0.1% (w/v).

In another embodiment of any one of the above aspects, the TRPM8 antagonist is administered in combination with another agent.

Other embodiments are provided infra.

DETAILED DESCRIPTION

Figure 1:
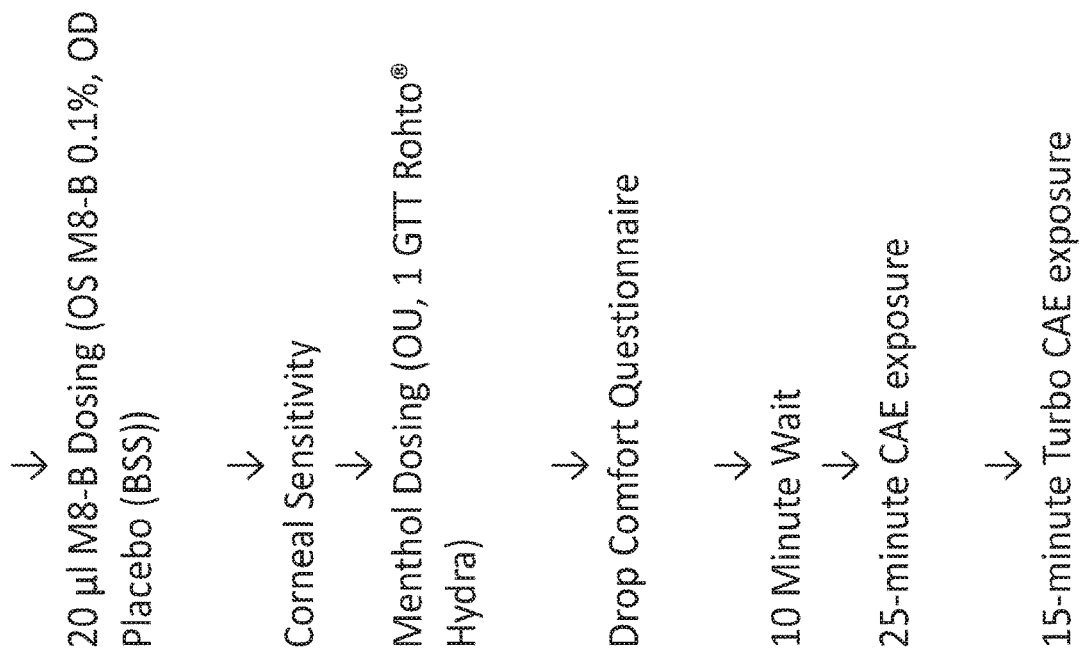
FIG. 1 is a schematic that shows the study design used in the experiments with the TRPM8 antagonist, Compound I.

The present invention is based on the surprising finding that a TRPM8 antagonist can block the effects of menthol, a known TRPM8 agonist, and further that the same TRPM8 antagonist can protect against ocular discomfort in models of dry eye and severe dry eye. The present invention reports the unexpected finding that a TRPM8 antagonist can reduce ocular discomfort, a finding that is contrary to results previously reported in the art that use TRPM8 agonists to reduce ocular discomfort via increasing tearing.

Accordingly, the invention described herein provides methods of treating or preventing an ocular disease or disorder in a subject comprising administering to the subject a composition comprising a pharmaceutically acceptable carrier and a pharmaceutically effective amount of a transient receptor potential melastatin 8 (TRPM8) antagonist. The invention also provides methods of treating or preventing ocular pain or discomfort in a subject comprising administering to the subject a composition comprising a pharmaceutically acceptable carrier and a pharmaceutically effective amount of a transient receptor potential melastatin 8 (TRPM8) antagonist.

Definitions

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to."

The term "or" is used herein to mean, and is used interchangeably with, the term "and/or," unless context clearly indicates otherwise.

The term "such as" is used herein to mean, and is used interchangeably, with the phrase "such as but not limited to."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "administer", "administering" or "administration" include any method of delivery of a pharmaceutical composition or agent into a subject's system or to a particular region in or on a subject. In certain embodiment, the composition is administered topically to the eye. The eye comprises a tissue or gland in or around the eye selected from the group consisting of ocular tissue, eyelids of the subject, ocular surface, meibomian gland and or lacrimal gland. Administration topically to the eye is meant to include administration to the eye or the area around the eye. Administering an agent can be performed by a number of people working in concert. Administering an agent includes, for example, prescribing an agent to be administered to a subject and/or providing instructions, directly or through another, to take a specific agent, either by self-delivery, or for delivery by a trained professional.

A "therapeutically effective amount" is that amount sufficient to treat a disease in a subject. A therapeutically effective amount can be administered in one or more administrations.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease or condition, stability (i.e., not worsening) state of disease or condition, amelioration or palliation of the disease state, and prevention of the disease state. Treatment does not need to be curative. Treatment can also refer to prevention of one or more signs or symptoms of an ocular disease or disorder.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the term "ocular disease or disorder" is meant to refer to any disease or disorder of or associated with the eye, including symptoms of the ocular disease or disorder.

As used herein, the term "dry eye disease" is meant to refer to an eye disease caused by decreased tear production or increased tear film evaporation. Other names for dry eye include dry eye syndrome, keratoconjunctivitis sicca (KCS), dysfunctional tear syndrome, lacrimal keratoconjunctivitis, evaporative tear deficiency, aqueous tear deficiency, and LASIK-induced neurotrophic epitheliopathy (LNE).

The term "ocular pain or discomfort" is meant to include, but not be limited to, ache, dryness or itchiness, a gritty sensation, redness, sensitivity to light, stinging or burning sensation or pain associated with the eye.

In certain embodiments, the dry eye disease or disorder is attributable to one or more causes selected from, but not limited to, aging, contact lens usage, environmental stress, fatigue, diet, hydration, systemic disease, visual tasking (such as reading or video screen use), inflammation or medication usage. In other embodiment, the dry eye disease is due to excessively fast tear evaporation (evaporative dry eyes) or inadequate tear production. In other embodiments, the dry eye disease is associated with refractive surgery.

The term "transient receptor potential melastatin 8 (TRPM8) antagonist" is meant to refer to any compound or any agent that can inhibit the activity of TRPM8 (i.e. block TRPM8-mediated signaling cascade) at an ophthalmically relevant concentration. TRPM8 antagonists useful in the methods of the invention include, but are not limited to, a small molecule, a nucleic acid molecule, an aptamer, an antisense molecule, an RNAi molecule, a protein, a peptide and an antibody or antibody fragment. Exemplary TRPM8 antagonists are described in WO2006040136, incorporated by reference in its entirety herein.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

I. Ocular Diseases or Disorders

The present invention provides methods of treating or preventing ocular diseases or disorders and methods of treating or preventing symptoms associated with ocular diseases or disorders.

Ocular diseases or disorders include any disease or disorder of or associated with the eye itself, or a tissue or gland in or around the eye, for example ocular tissue, eyelids of the subject, ocular surface, meibomian gland and or lacrimal gland.

An ocular disease or disorder that is treated or prevented by the methods of the present invention is dry eye disease. Other names for dry eye include dry eye syndrome, keratoconjunctivitis sicca (KCS), dysfunctional tear syndrome, lacrimal keratoconjunctivitis, evaporative tear deficiency, aqueous tear deficiency, and LASIK-induced neurotrophic epitheliopathy (LNE).

Dry eye disease is caused by an inadequate or altered tear film, and may be the result of an inability of the lacrimal glands to produce an adequate quantity of tears with the proper composition (Abelson et al. Curr Opin Ophthalmol 20: 282-286, 2009; Barabino and Dana Chem Immunol Allergy 92: 176-184, 2007). Alternatively, dry eyes may result from an inability of sensory afferent neurons to monitor the corneal surface, resulting in insufficient neuronal drive to produce a sufficient quantity of tears (Dartt Ocul Surf 2: 76-91, 2004, Prog Retin Eye Res 28: 155-177, 2009; Mathers CLAO J 26: 159-165, 2000; van Bijsterveld et al. Br J Ophthalmol 87: 128-130, 2003). Corneal primary afferent neurons express a range of membrane channels, which corresponds to their physiological characteristics. The primary afferent neurons innervating the cornea regulate secretion of basal tearing with a relay through the spinal trigeminal nucleus. It has been proposed that polymodal nociceptors express channels responding to noxious chemical, thermal, and mechanical stimulation, including TRPV1, TRPA1, TRPV4, and acid sensing ion channels (ASIC) channels. In contrast, cold receptors express TRPM8 channels, which are sensitive to innocuous cooling (Meng and Kurose Experimental Eye Research 117 (2013) 79-87).

Furthermore, it has been proposed that even if the initial cause of dry eye is dysfunction of the lacrimal gland, it has been suggested that the dry eye condition itself may affect corneal afferents involved in tear regulation, initiating a vicious cycle that may lead to a further deterioration in lacrimal gland function and a worsening of the condition (Mathers, 2000).

Aqueous tear-deficient dry eye is a disorder in which the lacrimal glands fail to produce enough of the watery component of tears to maintain a healthy eye surface. Evaporative dry eye may result from inflammation of the meibomian glands, also located in the eyelids. These glands make the lipid or oily part of tears that slows evaporation and keeps the tears stable. Dry eye can be associated with inflammation of the surface of the eye, the lacrimal gland, or the conjunctiva; any disease process that alters the components of the tears; an increase in the surface of the eye, as in thyroid disease when the eye protrudes forward; cosmetic surgery, if the eyelids are opened too widely.

Symptoms of dry eye include, but are not limited to stinging or burning of the eye; a sandy or gritty feeling as if something is in the eye; episodes of excess tears following very dry eye periods; a stringy discharge from the eye; pain and redness of the eye; episodes of blurred vision; heavy eyelids; inability to cry when emotionally stressed; uncomfortable contact lenses; decreased tolerance of reading, working on the computer, or any activity that requires sustained visual attention; eye fatigue.

Dry eye can be a temporary or chronic condition. Severe dry eye is a debilitating disease that affects millions of patients worldwide and can cripple some patients. Millions of these individuals suffer from the most severe form. This disease often inflicts severe ocular discomfort, results in a dramatic shift in quality of life, induces poor ocular surface health, substantially reduces visual acuity and can threaten vision. Patients with severe dry eye develop a sensitivity to light and wind that prevents substantial time spent outdoors, and they often cannot read or drive because of the discomfort.

The following are non-limiting examples of causes and symptoms of ocular diseases or disorders, such as ocular discomfort, and dry eye or severe dry eye. Ocular discomfort and/or dry eye can be a side effect of some medications, including antihistamines, nasal decongestants, tranquilizers, certain blood pressure medicines, Parkinson's medications, birth control pills and anti-depressants. Environmental stress dry environments or with moving air is a big factor in causing ocular discomfort and dry eye. Aging is one of the most common causes of ocular discomfort and/or dry eyes. About half of all people who wear contact lenses complain of ocular discomfort and/or dry eyes. Skin disease on or around the eyelids can result in ocular discomfort and/or dry eye. Diseases of the glands in the eyelids, such as meibomian gland dysfunction, can cause ocular discomfort and/or dry eye. Ocular discomfort and/or dry eye can occur in women who are pregnant. Women who are on hormone replacement therapy may experience ocular discomfort and/or dry eye symptoms. Ocular discomfort and/or dry eye can also develop after the refractive surgery known as LASIK. Symptoms of dry eye associated with refractive surgery have been reported to last in some cases from six weeks to six months or more following surgery. Ocular discomfort and/or dry eye can result from chemical and thermal burns that scar the membrane lining the eyelids and covering the eye. Allergies can be associated with ocular discomfort and/or dry eye. Infrequent blinking, associated with staring at computer or video screens or other visual tasks like reading, may also lead to ocular discomfort and/or dry eye symptoms. Both excessive and insufficient dosages of vitamins can contribute to ocular discomfort and/or dry eye. Loss of sensation in the cornea from long-term contact lens wear can lead to ocular discomfort and/or dry eye. Ocular discomfort and/or dry eye can be associated with immune system disorders such as Sjögren's syndrome, lupus, and rheumatoid arthritis. Sjögren's leads to inflammation and dryness of the mouth, eyes, and other mucous membranes. It can also affect other organs, including the kidneys, lungs and blood vessels. Ocular discomfort and/or dry eye can be a symptom of chronic inflammation of the conjunctiva, the membrane lining the eyelid and covering the front part of the eye, or the lacrimal gland. Ocular discomfort and/or inflammation can be caused by certain eye diseases, infection, exposure to irritants such as chemical fumes and tobacco smoke, or drafts from air conditioning or heating. If the surface area of the eye is increased, as in thyroid disease when the eye protrudes forward or after cosmetic surgery if the eyelids are opened too widely, ocular discomfort and/or dry eye can result. Ocular discomfort and/or dry eye may occur from exposure keratitis, in which the eyelids do not close completely during sleep.

II. TRPM8 Antagonists

Transient Receptor Potential (TRP) channels are one of the largest group of ion channels and, based on their sequence homology, are classified into 6 sub-families (TRPV, TRPM; TRPA, TRPC, TRPP and TRPML). TRP channels are cation-selective channels activated by several physical (such as temperature, osmolarity and mechanical stimuli) and chemical stimuli. TRPM8, which was cloned in 2002, is a non-selective cation channel of the TRP family. TRPM8 is located on primary nociceptive neurons (A-delta and C-fibers) and is also modulated by inflammation-mediated second messenger signals (Abe, J., et al., Neurosci Lett 2006, 397(1-2), 140-144; Premkumar, L. S., et al., J. Neurosci, 2005, 25(49), 11322-1 1329). It is activated by mild cold temperatures and synthetic cool-mimetic compounds such as menthol, eucalyptol and icilin (McKemy D. D. et al., Nature (2002) 416, 52-58; Peier A. M. et al. Cell (2002) 108, 705-715). Like several other TRP channels, TRPM8 is also gated by voltage (Nilius B. et al., J. Physiol. (2005) 567, 35-44). The voltage dependence of TRPM8 is characterized by a strong outward rectification at depolarized transmembrane potential and a rapid and potential-dependent closure at negative membrane potentials. Cooling agents and menthol application shifts the activation curve towards more negative potentials, increasing the possibility for the opening of the channel and boosting inward currents at physiological membrane potentials. Other endogenous factors, such as phospholipase A2 products (Vanden Abeele F. et al., J. Biol. Chem. (2006) 281, 40174-40182), endocannabinoids (De Petrocellis L et al., Exp. Cell. Res. (2007) 313, 1911-1920) and PIP2 (Rohacs T. et al., Nat. Neurosci. (2005) 8, 626-634) also participate in channel regulation.

The present invention is based on the surprising finding that a TRPM8 antagonist can block the effects of menthol, a known TRPM8 agonist, and further that the same TRPM8 antagonist can protect against ocular discomfort in models of dry eye and severe dry eye. The present invention reports the unexpected finding that a TRPM8 antagonist can reduce ocular discomfort, a finding that is contrary to the results previously reported in the art. Indeed, it has been proposed that activation of corneal cool cells via a TRPM8 channel agonist may represent a potential therapeutic intervention to treat dry eye by increasing tearing (Hirata and Meng Invest Ophthalmol Vis Sci 51, 2010; Parra et al. Nature Medicine, vol. 16(12), 2010; Robbins et al. Invest Ophthalmol Vis Sci 53, 2012).

TRPM8 antagonists can include, but are not limited to small molecules, nucleic acid molecules, aptamers, antisense molecules, RNAi molecules, proteins, peptides and antibodies or antibody fragments.

Small Molecule Inhibitors

Several classes of non-peptide TRPM8 antagonists have been disclosed. International patent application WO 2006/040136 describes substituted 4-benzyloxy-phenylmethyl-amide derivatives as cold menthol receptor-1 (CMR-I) antagonists for the treatment of urological disorders. International patent applications WO 2007/0 17092A1, WO 2007/017093A1 and WO 2007/0 17094A1 describe benzyloxyphenylmethyl carbamate, substituted 2-benzyloxybenzoic acid amide and substituted 4-benzyloxybenzoic acid amide derivatives for the treatment of diseases associated with the cold menthol receptor (CMR), a.k.a. TRPM8; WO 2007/134107 describes phosphorous-bearing compounds as TRPM8 antagonists for the treatment of TRPM8-related disorders; WO 2009/012430 describes sulfonamides for the treatment of diseases associated with TRPM8; WO 2010/103381 describes the use of spirocyclic piperidine derivatives as TRPM8 modulators in prevention or treatment of TRPM8-related disorders or diseases; and, WO 2010/125831 describes sulfamoyl benzoic acid derivatives as modulators of the TRPM8 receptor and their use in the treatment of inflammatory, pain and urological disorders.

Other TRPM8 inhibitors include AMTB (N-(3-aminopropyl)-2-[(3-methylphenyl)me thoxy]-N-(2-thienylmethyl)-benzamidehydrochloride (1:1) hyclate) (CAS 926023-82-7) (Santa Cruz Biotechnology, sc-361103) and JNJ41876666 (compound 5 in Parks D. J. et al., 2011, J Med Chem 54: 233-247); 3-[7-Trifluoromethyl-5-(2-trifluoromethyl-phenyl)-1H-benzimidazol-2-yl]-1-oxa-2-aza-spiro[4.5]dec-2-eneHydrochloride). BCTC, thio-BCTC, and capsazepine were identified as antagonists of the TRPM8 receptor. These antagonists physically block the receptor for cold and menthol, by binding to the S1-S4 voltage-sensing domain, preventing response (Behrendt H. J. et al., Br. J. Pharmacol. 141 (4): 737-45).

In certain preferred embodiments of the invention, the TRPM8 antagonist is a small molecule inhibitor.

Parks D. J. et al., J. Med. Chem. 2011, 54, 233-247 describe the design, synthesis, and optimization of a class of selective TRPM8 antagonists based on a benzimidazole scaffold.

In exemplary embodiments, the TRPM8 antagonist is the commercially available TRPM8 antagonist N-(2-Aminoethyl)-N-(4-(benzyloxy)-3-methoxybenzyl)thiophene-2-carboxamide hydrochloride, N-(2-Aminoethyl)-N-[[3-methoxy-4-(phenylmethoxy)phenyl]methyl]-2-thiophenecarboxamide hydrochloride (Sigma Aldrich M8-B hydrochloride (SML0893)), shown below as Compound I

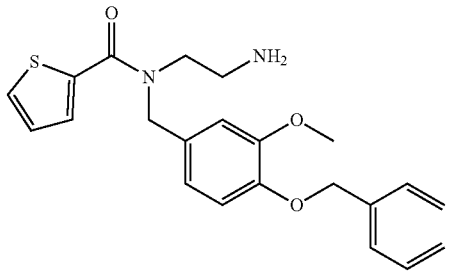

Compound I

Nucleic Acid Inhibitors
Antisense Molecules

The TRPM8 antagonist can be an antisense molecule that reduces transcription and/or translation of a component of TRPM8 activity. The antisense molecule comprises RNA or DNA prepared using antisense technology, where, for example, an antisense RNA or DNA molecule acts to block directly the translation of mRNA by hybridizing to targeted mRNA and preventing protein translation. Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such oligonucleotides can also be delivered to cells such that the antisense RNA or DNA may be expressed in vivo to inhibit production of components TRPM8 activity.

TRPM8 antagonists include antisense or sense oligonucleotides comprising a single-stranded nucleic acid sequence (either RNA or DNA) capable of binding to target mRNA (sense) or DNA (antisense) sequences. Such a fragment generally comprises about 10 to 40 nucleotides in length, preferably at least about 14 nucleotides, preferably from about 14 to 30 nucleotides.

Antisense or sense oligonucleotides further comprise oligonucleotides having modified sugar-phosphodiester backbones that are resistant to endogenous nucleases, or are covalently linked to other moieties that increases affinity of the oligonucleotide for a target nucleic acid sequence, or intercalating agents to modify binding specificities of the antisense or sense oligonucleotide for the target nucleotide sequence.

Small Interfering RNA (siRNA)

siRNA can be used as a TRPM8 antagonist, for example to inhibit TRPM8 activity. "siRNA" or "RNAi" are double-stranded RNA molecules, typically about 21 nucleotides in length, that are homologous to a gene or polynucleotide that encodes the target gene and interfere with the target gene's expression.

Nucleic Acid Molecules in Triple-Helix Formation

Nucleic acid molecules in triple-helix formation can be used as a TRPM8 antagonist. Nucleic acid molecules in triple-helix formation used to inhibit transcription should be single-stranded and composed of deoxynucleotides. A DNA oligonucleotide is designed to be complementary to a region of the gene involved in transcription. The base composition of these oligonucleotides is designed such that it promotes triple-helix formation via Hoogsteen base-pairing rules, which generally require sizeable stretches of purines or pyrimidines on one strand of a duplex.

Ribozymes

Ribozymes can be used as a TRPM8 antagonist. A "ribozyme" is an enzymatic RNA molecule capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques.

Antibodies

The term "antibody" is used in the broadest sense and specifically covers, for example, polyclonal antibodies, monoclonal antibodies (including antagonist and neutralizing antibodies), antibody compositions with polyepitopic specificity, single chain antibodies, and fragments of antibodies, provided that they exhibit the desired activity of a TRPM8 inhibitor. Antagonistic TRPM8 antibodies are useful in the methods of the invention. An antibody inhibitor will specifically bind to a particular polypeptide or epitope on a particular polypeptide without substantially binding to any other polypeptide or polypeptide epitope. Such binding will partially or fully block, neutralize, reduce or antagonize TRPM8 activity.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. Generally, the antibody will be purified (1) to greater than 95% by weight of antibody as determined by the Lowry method, and most preferably more than 99% by weight, (2) to a degree sufficient to obtain at least 15 residues of N terminal or internal amino acid sequence by use of a spinning cup sequenator, or (3) to homogeneity by SDS PAGE under reducing or non-reducing conditions using Coomassie blue or, preferably, silver stain. An isolated antibody includes the antibody in situ within recombinant cells since at least one component of the antibody's natural environment will not be present. Ordinarily, however, isolated antibody will be prepared by at least one purification step.

Where antibody fragments are used, the smallest inhibitory fragment that specifically binds to the target TRPM8 protein is preferred.

Various inhibitory TRPM8 antibodies are known in the art and are commercially available, for example from Santa Cruz Biotechnology TRPM8 (G-16), TRPM8 (N-15) or TRPM8 (D-25).

The term antibody is meant to include polyclonal antibodies, monoclonal antibodies, humanized antibodies, chimeric antibodies, antibody fragments, single chain antibodies, diabodies, bispecific antibodies and multivalent antibodies.

III. Methods

The present invention provides methods of treating or preventing an ocular disease or disorder in a subject comprising administering to the subject a composition comprising a pharmaceutically acceptable carrier and a pharmaceutically effective amount of a transient receptor potential melastatin 8 (TRPM8) antagonist.

Treating or preventing the ocular disease or disorder is meant to encompass treating or preventing the symptoms of the ocular disease or disorder.

The present invention also features methods of treating or preventing ocular pain or discomfort in a subject comprising administering to the subject a composition comprising a pharmaceutically acceptable carrier and a pharmaceutically effective amount of a transient receptor potential melastatin 8 (TRPM8) antagonist.

The ocular pain may be caused by a dry eye disease.

The corneal pain system is unique in its principal role of protecting, sustaining and restoring the optical tear layer without which our vision would be non-functional. To meet this existential need, the human dry eye alarm evolved into the most powerful, sensitive and complex pain system in the body, incorporating sensors that are unusually vulnerable to being exposed to the noxious environment. Like other damaged nociceptive systems, it is capable of failing and becoming a disease in its own right known as neuropathic pain (Treede R. D. et al., Neurology 2008; 70:1630-5). Indeed, the features of corneal nerves associated with pain parallel the well-defined properties of somatic neuropathic pain defined as ongoing pain as a direct consequence of a lesion or disease affecting the somatosensory system.

Dry eye-like pain is a unique type of corneal pain that is associated with excessive tear film evaporation. Unlike pain experienced elsewhere in the body, that of dry eye is characterised by its sensitivity to environmental evaporative factors in being exacerbated by circumstances that promote tear film evaporation and are mitigated by those that suppress it. Thus, in addition to mechanisms commonly associated with neuropathic pain, specialised corneal nociceptors tuned to tear film evaporation have been shown to play a central role in generating chronic sensations of dry eye.

Also provided by the present invention are methods of normalizing the tear film in a subject comprising administering to the subject a composition comprising a pharmaceutically acceptable carrier and a pharmaceutically effective amount of a transient receptor potential melastatin 8 (TRPM8) antagonist.

The tear film is made up of three layers: an oil (lipid) layer, a water (aqueous) layer and a mucin layer. When any part of the tear film is not functioning properly, one or more Dry Eye symptoms may occur. To evaluate the normalization of the tear film (tear film normalization test) can be used as a diagnostic test for dry eye syndrome. The tear film normalization test is described in the art, for example in Latkany et al., (Cornea. 2006 December; 25(10): 1153-7).

In the methods of the present invention, the eye is meant to comprise a tissue or gland in or around the eye selected from the group consisting of ocular tissue, eyelids of the subject, ocular surface, meibomian gland and or lacrimal gland of the human.

In some embodiments, these methods are performed by a medical professional (e.g., a physician, a physician's assistant, a nurse, a nurse's assistant, or a laboratory technician). In other embodiments, these methods are performed by the subject on himself. In some embodiments, the subject may already be taking one or more pharmaceutical agents for treatment of dry eye and the compositions of the present invention are administered to the subject in combination with the one or more pharmaceutical agents previously taken by the subject.

IV. Dosage and Administration

As demonstrated herein, a TRPM8 antagonist can protect against ocular discomfort in models of dry eye and severe dry eye. The present invention provides methods of treating or preventing an ocular disease or disorder in a subject comprising administering to the subject a composition comprising a pharmaceutically acceptable carrier and a pharmaceutically effective amount of a transient receptor potential melastatin 8 (TRPM8) antagonist. The invention also features methods of normalizing the tear film in a subject comprising administering to the subject a composition comprising a pharmaceutically acceptable carrier and a pharmaceutically effective amount of a transient receptor potential melastatin 8 (TRPM8) antagonist. In certain embodiments, the TRPM8 antagonist can be administered to a subject wherein at least one additional agent for the treatment of an ocular disease or disorder, for example dry eye, is administered to the subject. As used herein, the agents can be administered sequentially, in either order, or at the same time. Administration of multiple agents to a subject does not require co-formulation of the agents or the same administration regimen.

The pharmaceutically effective amount of the TRPM8 antagonist in the composition varies depending on the TRPM8 antagonist employed. In certain embodiments, the pharmaceutically effective amount of the TRPM8 antagonist is 0.001-5.0% (w/v). In exemplary embodiments, the pharmaceutically effective amount of the TRPM8 antagonist is 0.1% (w/v).

The pH of the composition of the present invention is not particularly restricted as long as it is within the ophthalmologically acceptable range, and it is usually adjusted to 4.0-7.0. The osmotic pressure of the aqueous suspension formulation of the invention is not limited as far as it is physiologically acceptable. For example, in case that the aqueous suspension formulation of the invention is used in ophthalmic formulation, the osmotic pressure of the formulation used is generally 150-600 mOsm/kg, for example 200-400 mOsm/kg, or for example 245-365 mOsm/kg. The osmotic pressure can be adjusted by any manner known in the art.

Preferably, the composition of the present invention is administered topically to the eye, for example administered to the eye or around the eye. The composition may be in the form of a solid, a paste, an ointment, a gel, a liquid, an aerosol, a mist, a polymer, a film, an emulsion, or a suspension.

Pharmaceutically Acceptable Carriers

Suitable ophthalmic carriers are known to those skilled in the art and all such conventional carriers may be employed in the present invention. The compositions of the present invention may further contain various additives such as buffering agents, isotonizing agents, solubilizers, preservatives, viscosity-increasing agents, chelating agents, and pH regulators.

Exemplary compounds incorporated to facilitate and expedite transdermal delivery of topical compositions into ocular tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), polysaccharides (sugars or gums, such as hyaluronic acid (HA), hydroxypropyl methylcellulose (HPMC), hydroxyethylcellulose (HEC), methylcellulose, guar gum, cellulose gum), sulfoxide (dimethylsulfoxide and decylmethylsulfoxide), amide (urea, dimethylacetamide and pyrrolidone derivatives), surfactant (sodium lauryl sulfate, cetyltrimethylammonium bromide, polaxamers, spans, tweens, bile salts and lecithin), terpene (d-limonene, alphaterpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist. Thus, a particular carrier may take the form of a sterile, ophthalmic ointment, cream, gel, solution, or dispersion. Also including as suitable ophthalmic carriers are slow release polymers, e.g., "Ocusert" polymers, "Hydron" polymers, etc.

Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chlorbutanol, benzalkonium chloride, cetylpyridium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcelullose, glycerine and EDTA. The solutions are preferably maintained at substantially neutral pH and isotonic with appropriate amounts of conventional buffers, e.g., phosphate, borate, acetate, tris.

The compositions of the present invention can be incorporated into formulations such as medicaments and ointments known in the art, including eye drops, artificial tears, eyewashes, including eyewashes which can wash the eyes while wearing contact lenses, compositions for contact lenses (solutions for wearing contact lenses, compositions for contact lenses care (disinfectant solutions for contact lens, storage solutions for contact lens, cleansing solutions for contact lenses, cleansing-storage solutions for contact lenses).

In certain embodiments of the present invention, the compositions can be incorporated into a hydrogel for delivery to the eye. Exemplary hydrogels are described in U.S. Pat. No. 9,125,807, incorporated by reference in its entirety herein.

Combination Treatment

The compositions of the invention may be administered in combination with other agents. Any agent known in the art is encompassed by the present invention. Exemplary agents include anesthetics, analgesics, antiallergenics, antihistamines, anti-inflammatory agents, anti-cancer agents, antibiotics, antiinfectives, antibacterials, anti-fungal agents, antiviral agents, cell transport/mobility impending agents, antiglaucoma drugs, mucomimetics, mucogenics, secretagogues, demulcents, wetting agents, lubricants, hypertensives, decongestants, immunological response modifiers, immunosuppresive agents, peptides, proteins, steroidal compounds, steroids, low solubility steroids, carbonic anhydrize inhibitors, diagnostic agents, antiapoptosis agents, gene therapy agents, sequestering agents, reductants, antipermeability agents, antisense compounds, antiproliferative agents, antibodies, antibody conjugates, bloodflow enhancers, antiparasitic agents, non-steroidal anti inflammatory agents, nutrients, vitamins, enzyme inhibitors, antioxidants, anticataract drugs, aldose reductase inhibitors, cytoprotectants, cytokines, cytokine inhibitors, cytokine protectants, UV blockers, mast cell stabilizers, anti neovascular agents, antiangiogenic agents, matrix metalloprotease inhibitors, vascular endothelial growth factor (VEGF) modulators, neuroprotectants, miotics, anti-cholinesterase, mydriatics and ocular lubricants and artificial tear/dry eye therapies.

V. Animal Models

A number of animal models of that mimic the different pathophysiologic mechanisms of dry eye have been described (Schrader S. et al., Dev Ophthalmol 2008, 41:298-312). Some of those models include the hereditary mouse models resembling Sjögren's syndrome (Schenke-Layland K. et al., Exp Eye Res 2010, 90(2):223-237; Lavoie T. N. et al., J Biomed Biotechnol 2011, 2011:549107), the mouse model induced by botulinum toxin B (Suwan-apichon O. et al., Invest Ophthalmol Vis Sci 2006, 47(1):133-139) or controlled environment (Chen W. et al., Invest Ophthalmol Vis Sci 2008, 49(4):1386-1391), rat models induced by evoked dacryoadenitis (Jiang G. Invest Ophthalmol Vis Sci 2009, 50(5):2245-2254) or anticholinergic drugs (Jain P. et al., Exp Eye Res 2011, 93(4):503-512), rabbit models induced by closure of the meibomian gland orifices (Gilbard J. P. et al., Ophthalmology 1989, 96(8):1180-1186), controlled environment (Fujihara T. et al., J Ocul Pharmacol Ther 1995, 11(4):503-508), evoked dacryoadenitis (Guo Z. et al., Exp Eye Res 2000, 71(1):23-31), preganglionic parasympathetic denervation (Toshida H. et al., Invest Ophthalmol Vis Sci 2007, 48(10):4468-4475), topical medication of a preservative (Xiong C. et al., Invest Ophthalmol Vis Sci 2008, 49(5):1850-1856) or removing of the lacrimal gland (Chen Z. Y. et al., Cornea 2011, 30(9):1024-1029), canine models formed spontaneously (Hick S. J. et al., Exp Eye Res 1998, 67(6):709-718) or induced by canine distemper virus (de Almeida D. E. et al., Vet Ophthalmol 2009, 12(4):211-215) and monkey models by removing the lacrimal gland (Francois J. et al., Ophthalmic Res 1976, 8:414-424).

Studies in rats have used lacrimal gland removal to produce a dry condition on the ocular surface (Fujihara T. et al., Invest Ophthalmol Vis Sci 42: 96-100, 2001; Kaminer et al., J Neurosci 31: 11256-11267, 2011).

Because rabbits have large eyes amenable to slit-lamp microscopic examinations, and considering their gentle nature and relatively low cost to maintain, rabbit models are well-suited to study the development of dry eye. In one rabbit model, the lacrimal gland is disabled and the Harderian gland and nicitating membrane are surgically removed simultaneously (Francois J. et al., 1976; Gilbard J. P. et al., Invest Ophthalmol Vis Sci 1987, 28(2):225-228; Gilbard J. P. Acta Ophthalmol Suppl 1989, 192:95-101). Another study (Xie H. P. et al., Chin Ophthalmic Res 1992, 10(1):10-12) established a dry eye model in rabbits by burning the bulbar conjunctiva with 50% trichloroacetic acid then surgically removing the lacrimal gland, Harderian gland, and nictitating membrane.

Rahman W. et al., Pain 156 (2015) 942-950 describe exorbital gland removal, a model for aqueous tear deficient dry eye, to determine the effects of persistent reduced tear volume on the properties of ocular-responsive neurons at the Vi/Vc transition and Vc/C1 regions and evoked eye blink behavior.

Depending on the specific animal model selected and the time of intervention, e.g., before or after the appearance of metabolic syndrome, the animal models can be used to demonstrate the efficacy of the methods provide herein for the treatment or prevention of ocular disorders such as dry eye and related symptoms.

VI. Kits

The present invention also features kits comprising a pharmaceutically effective amount of a transient receptor potential melastatin 8 (TRPM8) antagonist and a pharmaceutically acceptable carrier. The kits of the invention may also include instructions for use for treating or preventing an ocular disease or disorder, or treating or preventing ocular pain or discomfort, or increasing tear production in a subject.

EXAMPLES

A series of experiments were carried out assessing the clinical signs and symptoms of dry eye disease or severe dry eye disease using a commercially available TRPM8 antagonist, N-(2-Aminoethyl)-N-(4-(benzyloxy)-3-methoxybenzyl)thiophene-2-carboxamide hydrochloride, N-(2-Aminoethyl)-N-[[3-methoxy-4-(phenylmethoxy)phenyl]methyl]-2-thiophenecarboxamide hydrochloride (Sigma Aldrich M8-B hydrochloride (SML0893)), shown below as Compound I, at a concentration of 0.1% (vs placebo), administered unilaterally.

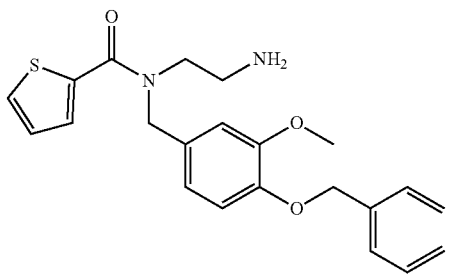

Compound I

A schematic outline of the study design is shown in FIG. 1. Post-dose, exposure to Menthol (ROHTO Hydra), as well as to an adverse environment (CAESM), was used to elicit symptomology in 3 patients with healthy eyes. Validated symptom scales were used to collect levels of discomfort secondary to the exposures (Ora Calibra™ Ocular Discomfort Questionnaire, Drop Comfort Questionnaire). A summary of the findings is presented below.

Example 1

Effect of Compound I on Corneal Sensitivity

Figure 2:
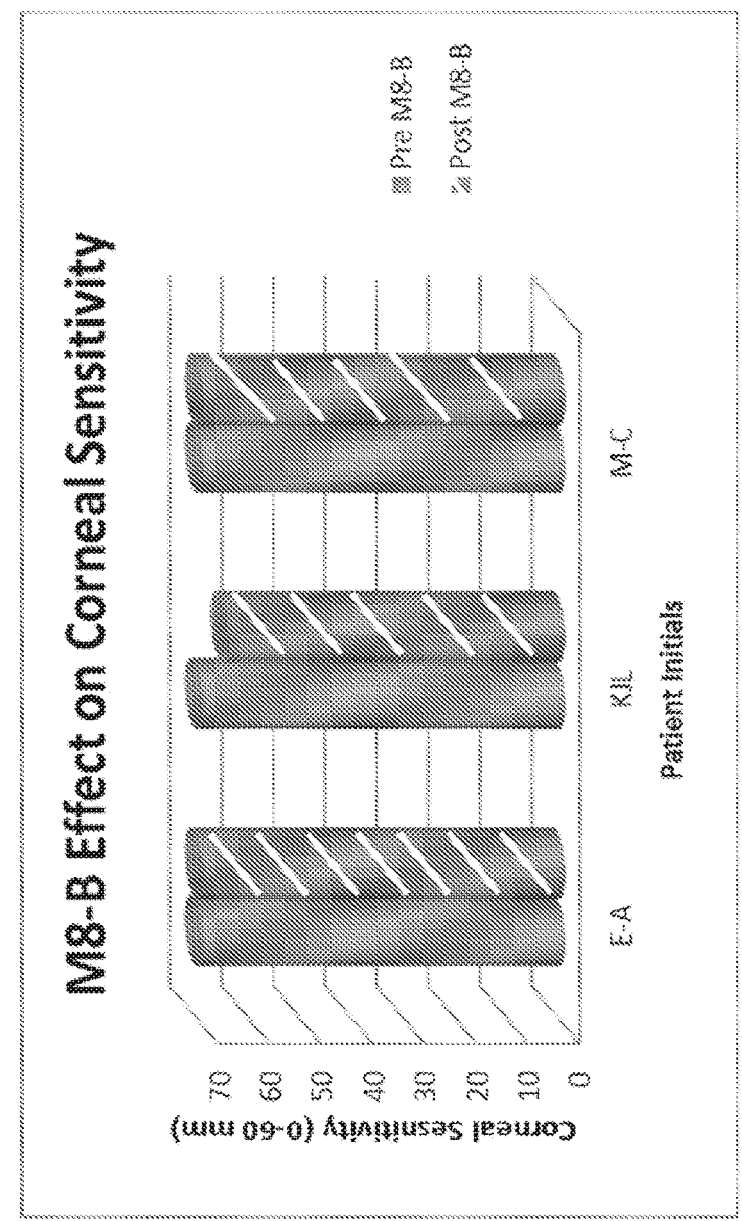
FIG. 2 is a graph that shows the effect of Compound I on corneal sensitivity.

In a first set of experiments, the effect of Compound I on corneal sensitivity was examined. Subjects (shown by initials E-A, KJL, M-C) were dosed with 20 ul of Compound I (0.1%) or a placebo (BSS). As shown in FIG. 2, Compound I had a minimal effect on corneal sensitivity, as measured by a Cochet Bonnet. Subject E-A and M-C had no detectable changes in sensitivity. Subject KJL had a 5 mm degrease in sensitivity (70 mm to 65 mm). No significant difference was found pre- to post-dose (p=0.42).

Example 2

Effect of Compound I on Post-Menthol Treatment Symptoms

Figure 3A:
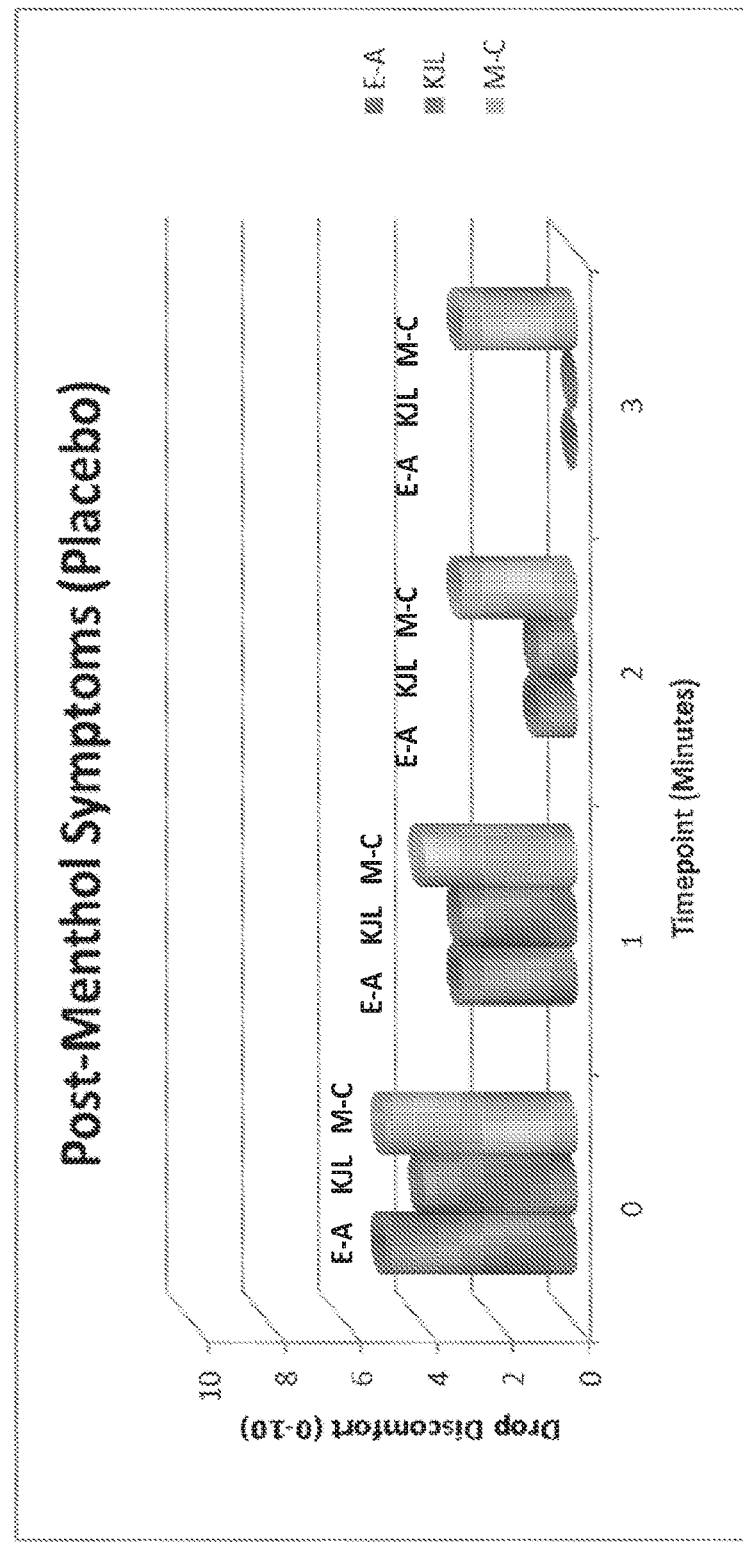
FIG. 3A and FIG. 3B are graphs that show post-menthol treatment symptoms after dosing with placebo (FIG. 3A) or Compound I (FIG. 3B). Subjects are shown by initials E-A, KJL, M-C.
Figure 3B:
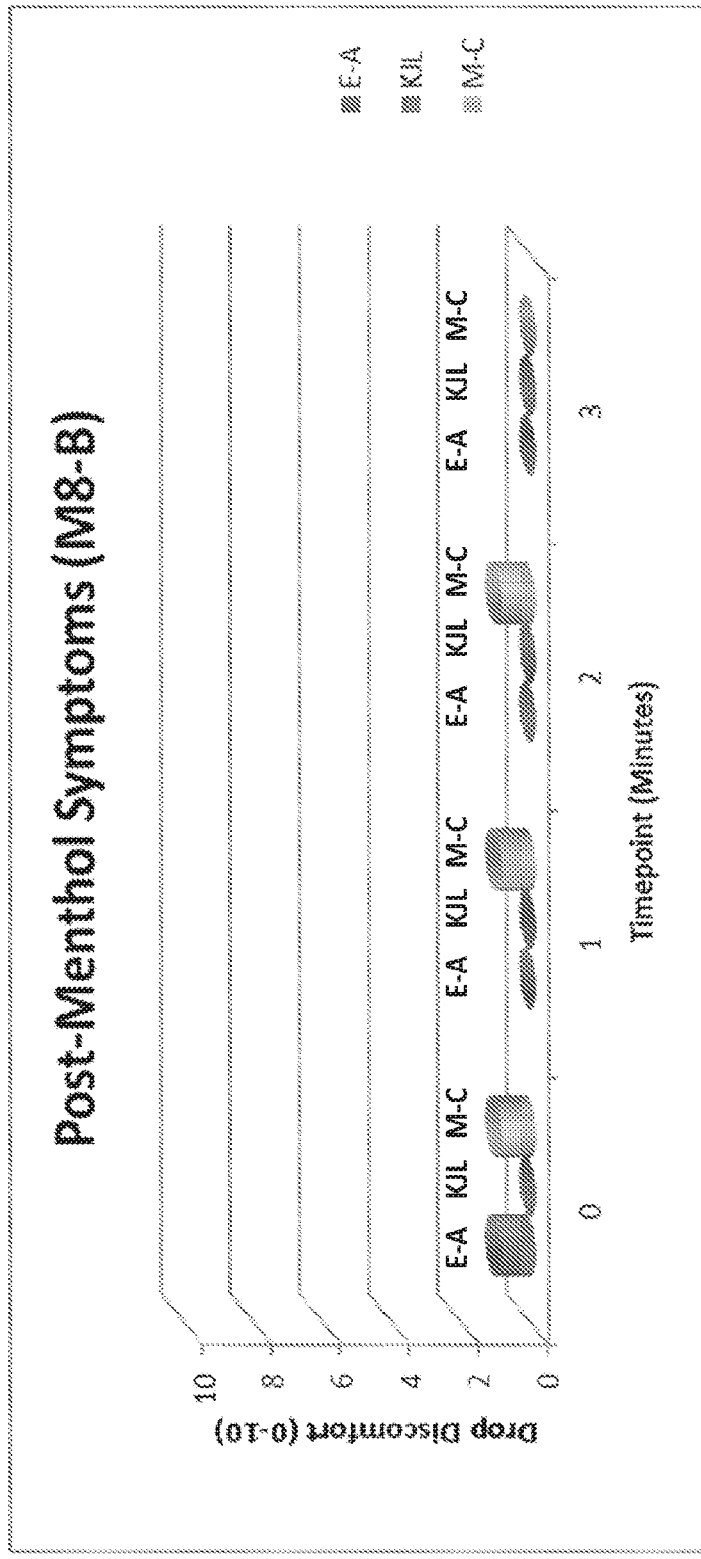

The effect of topical menthol application after dosing with Compound I or placebo was examined. After dosing with Compound I or placebo, 1 drop menthol-containing OTC eyedrop were administered bilaterally (ROHTO Hydra). Menthol is known to act upon TRPM-8 channels, effectively causing neural activity similar in nature to exposure to cold temperature. As such, menthol was used to induce a "cooling" symptom. As shown in FIGS. 3 A and B, Compound I was able to effectively block the action of menthol, by competing for TRPM-8 channels as an antagonist, resulting in diminished subject-reported symptoms (Drop Discomfort, 0-10 scale). The eye treated with Compound I had significantly lower symptom scores than placebo (p<0.01). Baseline (pre-menthol) symptoms were "0" for each eye, for all 3 subjects (data not shown).

Example 3

Effect of Compound I on Response to a Controlled Adverse Environment (CAE)

Figure 4A:
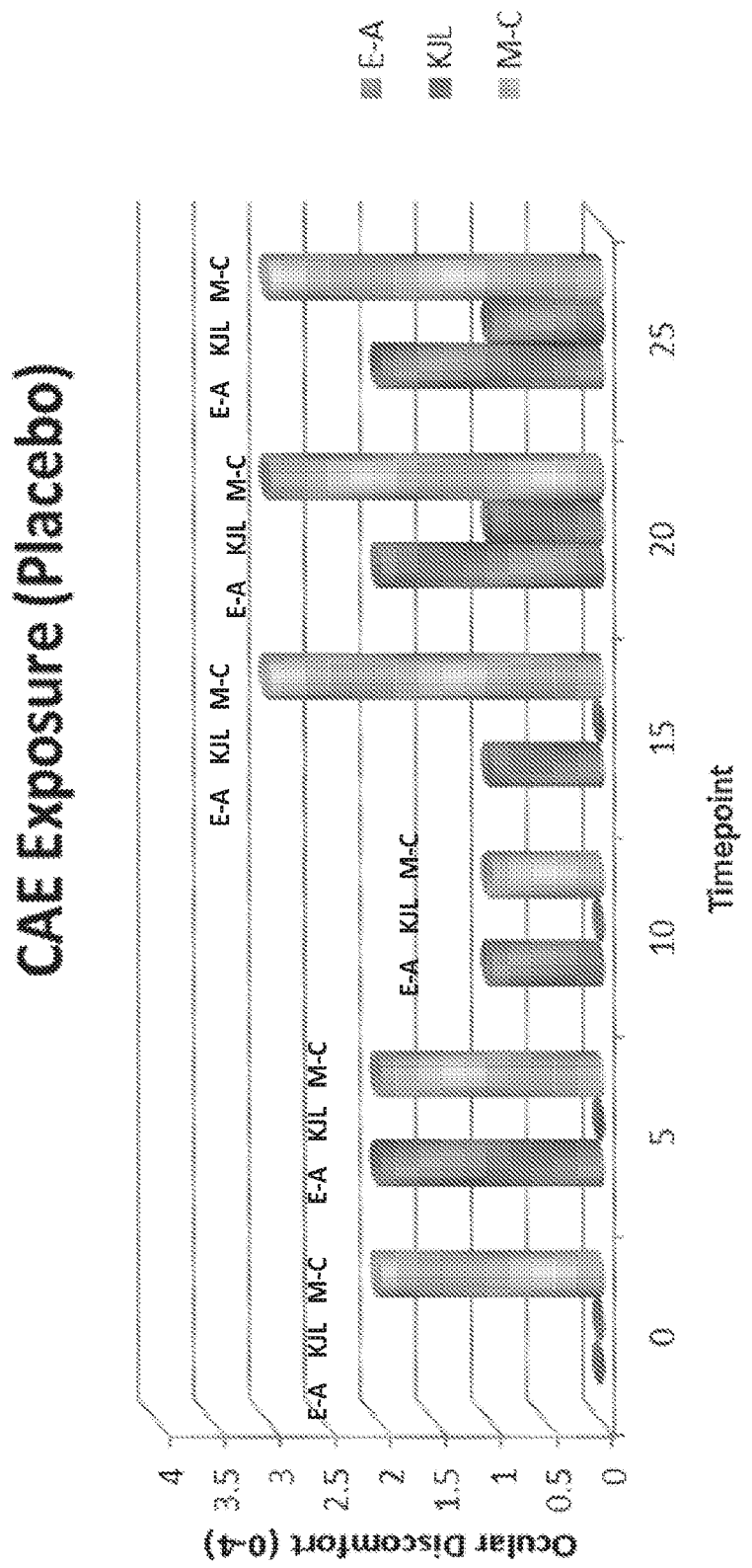
FIG. 4A and FIG. 4B are graphs that show effects on ocular discomfort after dosing with placebo (FIG. 4A) or Compound I (FIG. 4B) and exposure to a Controlled Adverse Environment (CAE).
Figure 4B:
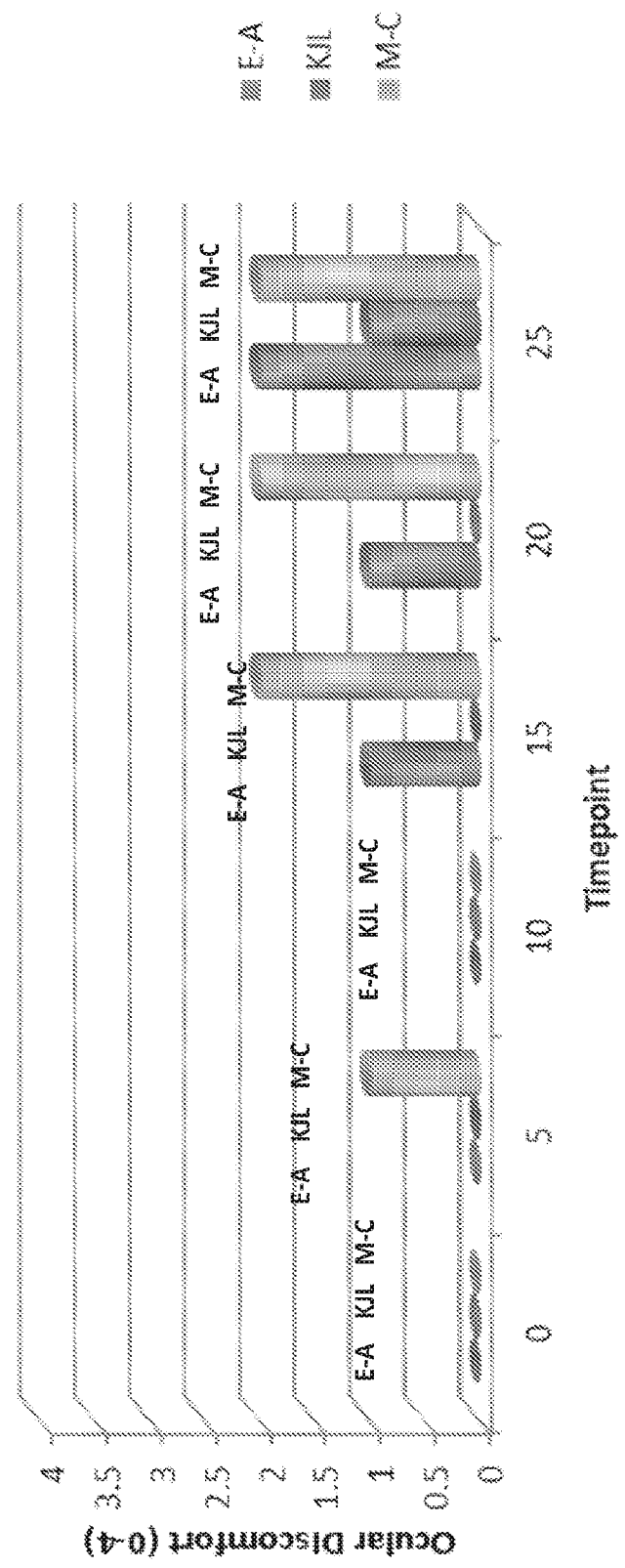

The effect of CAE exposure after dosing with Compound I or placebo was examined. After dosing with Compound I or placebo, subjects were exposed to a Controlled Adverse Environment (CAE) for 25 minutes, in order to elicit symptomology similar in nature to dry eye symptoms. An Ocular Discomfort Questionnaire (0-4 scale) was asked every 5 minutes. As shown in FIGS. 4 A and B, the eye treated with Compound I had significantly lower symptom scores than placebo (p<0.01).

Figure 5A:
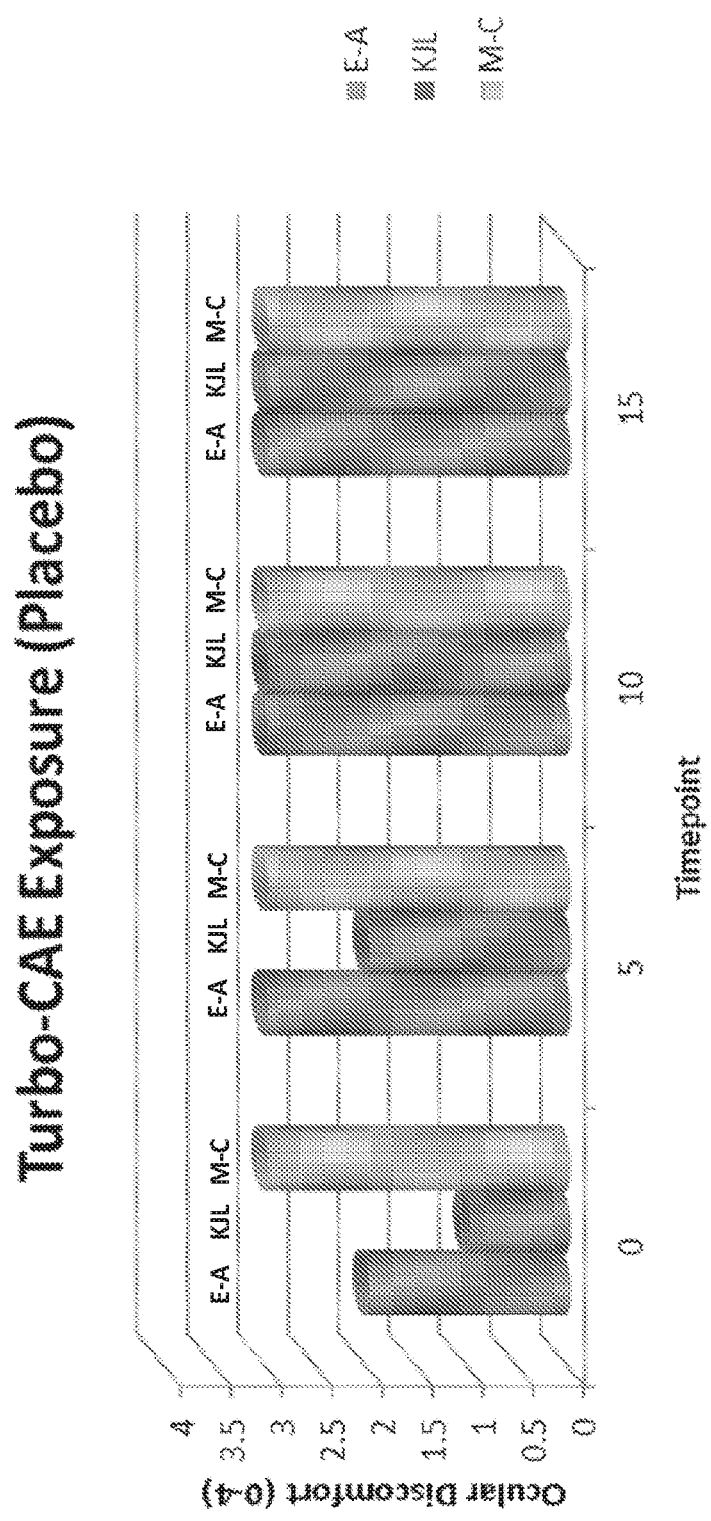
FIG. 5A and FIG. 5B are graphs that show effects on ocular discomfort after dosing with placebo (FIG. 5A) or Compound I (FIG. 5B) and exposure to and exposure to a Controlled Adverse Environment (CAE) and Turbo-CAE.
Figure 5B:
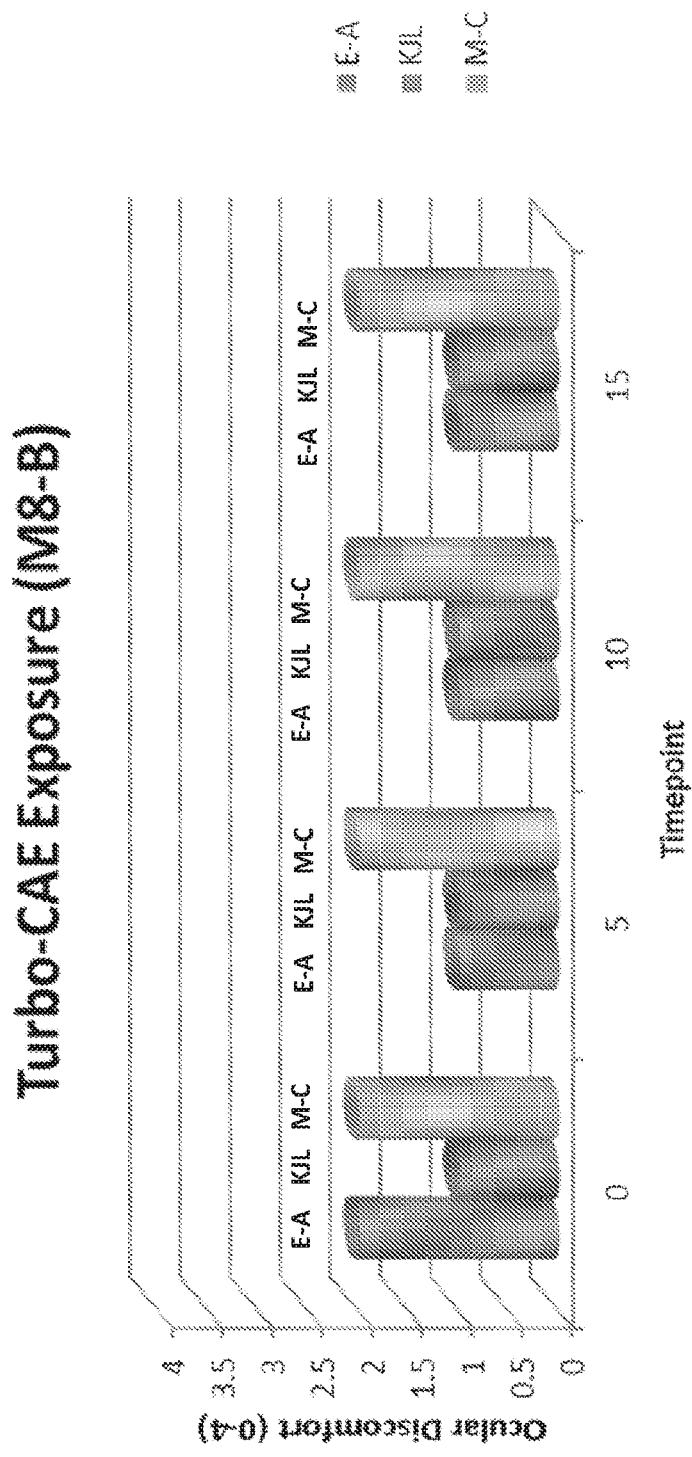

Next, the effect of Turbo-CAE exposure after dosing with Compound I or placebo was examined. After 25-minute Controlled Adverse Environment (CAE) exposure, subjects were exposed to 15 minutes of Turbo-CAE, in order to elicit symptomology similar in nature to severe dry eye symptoms. An Ocular Discomfort Questionnaire (0-4 scale) was asked every 5 minutes. As shown in FIGS. 5 A and B, the eye treated with Compound I had significantly lower symptom scores than placebo (p<0.01).

Example 4

Behavioral Endpoints

Figure 6:
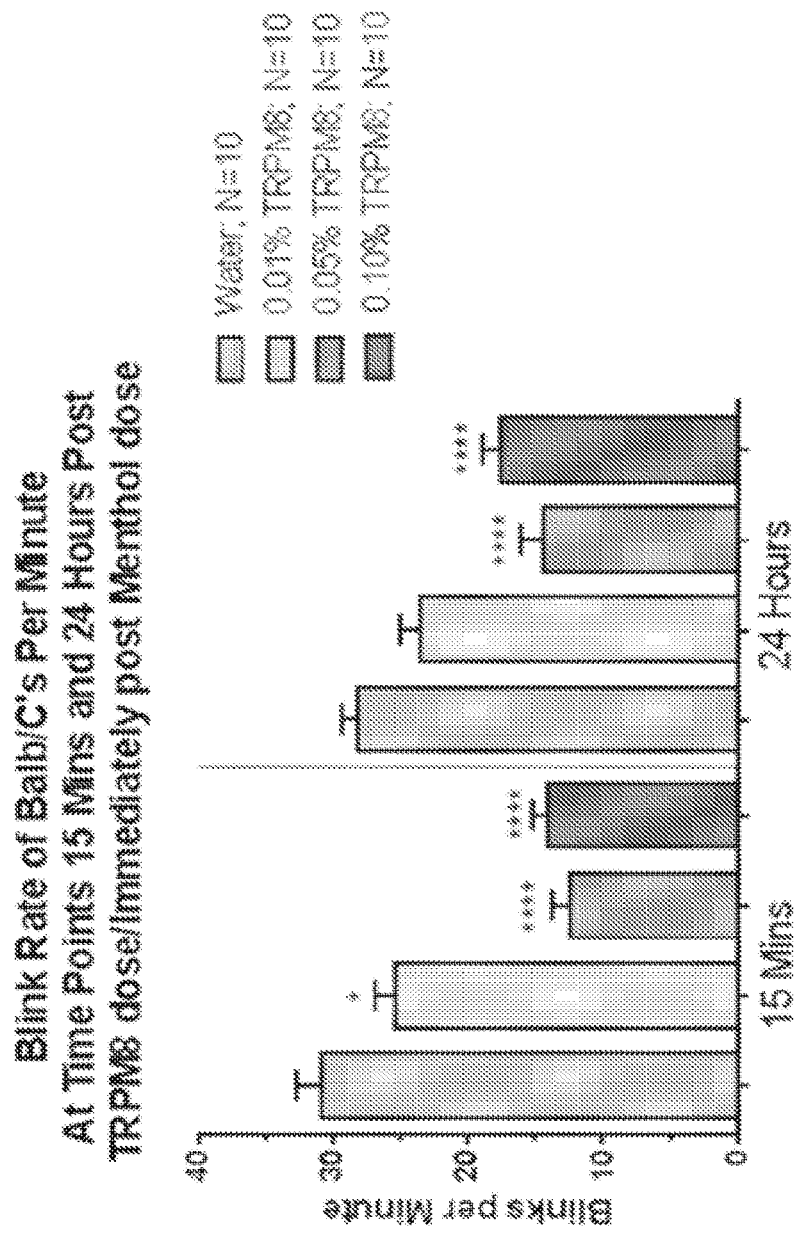
FIG. 6 is a graph that shows the blink rate of Balb/C's per minute at time points 15 minutes and 24 Hours post TRPM8 dose/immediately post menthol dose.

Behavioral endpoints, e.g. blinking for balb/cs nice, was tested. FIG. 6 is a graph that shows the blink rate of Balb/C's per minute at time points 15 minutes and 24 hours post TRPM8 antagonist dose and immediately post menthol dose. As shown in FIG. 6, menthol produces an increase in blink rate, which is reproducibly blocked by trpm8 antagonist. Treatment of the mice with water was used as a control. TRPM8 antagonist was used at concentrations of 0.01%, 0.05% and 0.10%.

Example 5

Tear Production

Figure 7:
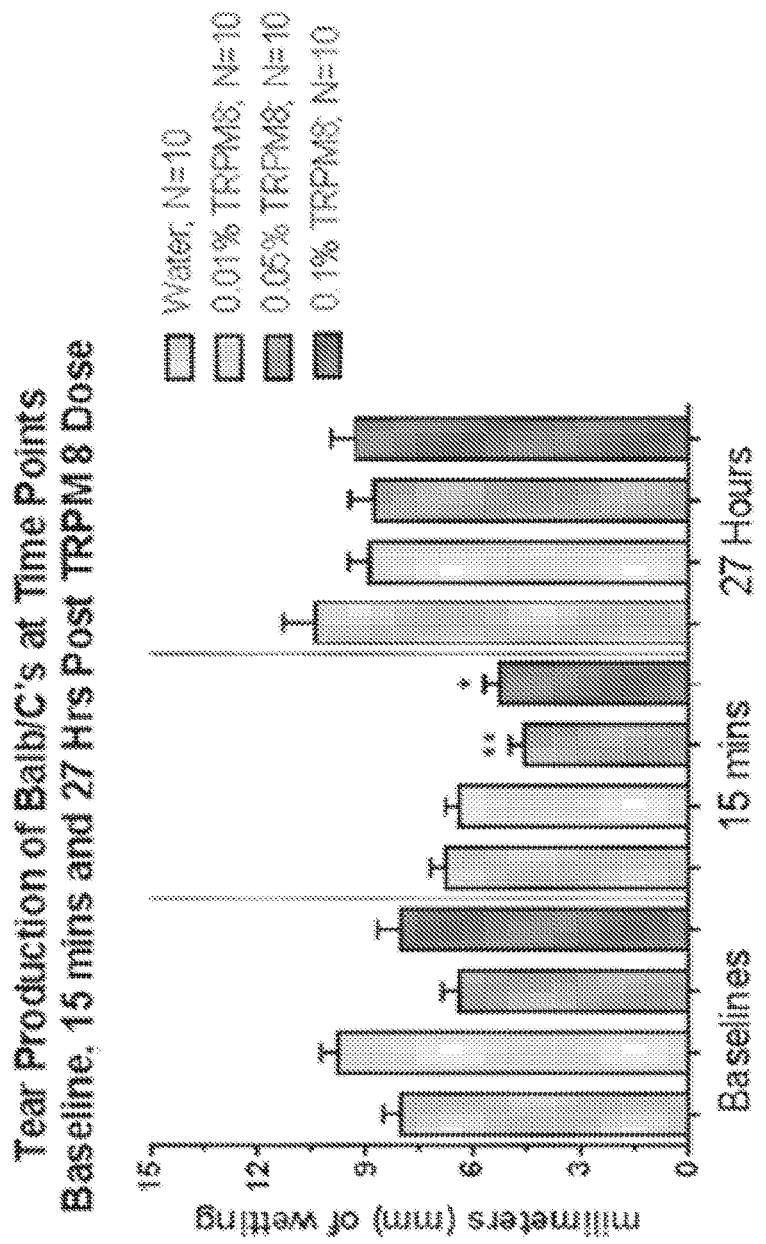
FIG. 7 is a graph that shows tear production of Balb/C's at time points 15 minutes and 27 hours post menthol dose.

FIG. 7 is a graph that shows tear production of Balb/C's at time points 15 minutes and 27 hours post menthol dose. Treatment of the mice with water was used as a control. TRPM8 antagonist was used at concentrations of 0.01%, 0.05% and 0.10%.

Figure 8:
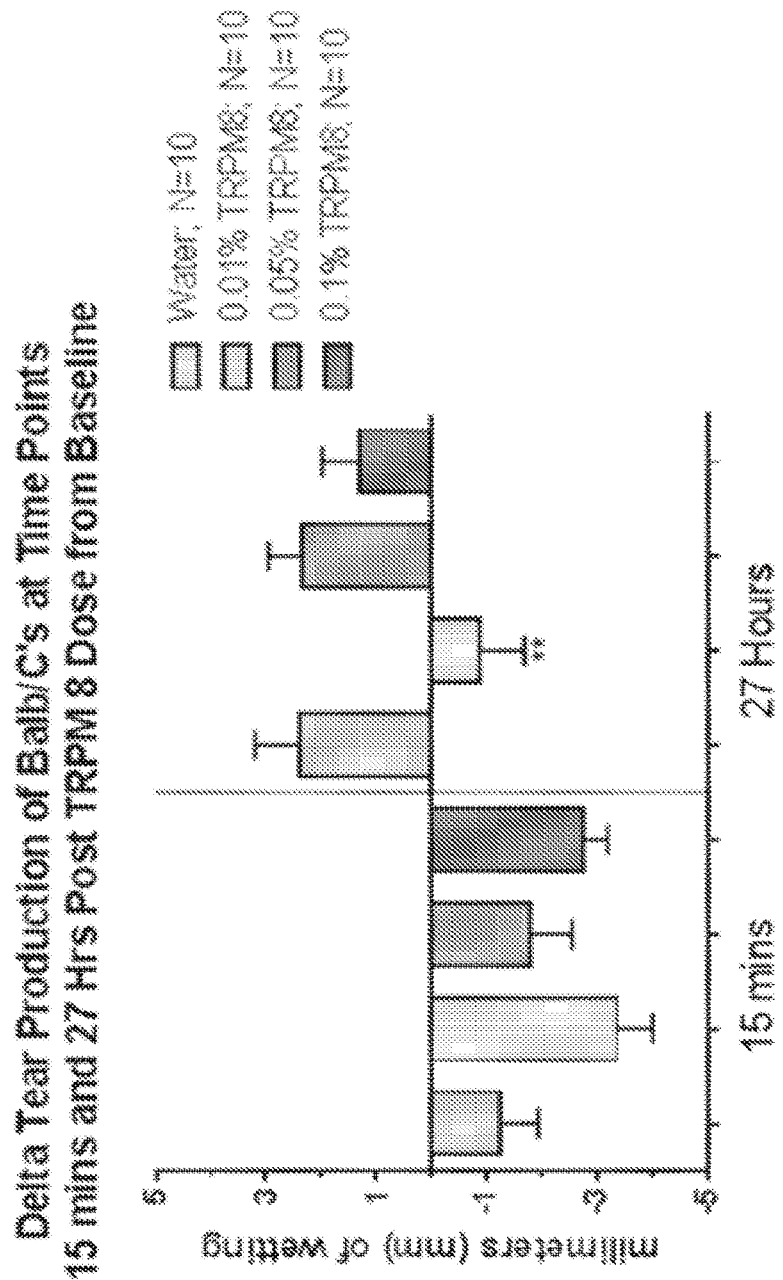
FIG. 8 is a graph that shows delta tear production of Balb/c's at time points 15 minutes and 27 hours post TRPM dose from baseline.

FIG. 8 is a graph that shows delta tear production of Balb/c's at time points 15 minutes and 27 hours post TRPM dose from baseline.

Experiments will be performed to test the same 4 groups of animals (water vehicle, 0.01%, 0.05%, and 0.1% TRPM8) in either a single dose, once daily multidose, or twice daily multi dose tear production test. The protocol for the single dose will be the same as described in FIG. 7 and FIG. 8; however measurements will be taken at the following time points: baseline, dose, 15 min, 1 hr, 8 hr, and 24 hours post dose. For once daily multidose testing, animals will be dosed once daily for 3 or 5 days. Baseline measurements will be performed before the first dose ever, then a measurement pre dose will be taken on the last day, then 15 min, 1 hr, 8 hr, and 24 hours post last dose. For twice daily multi dose testing, animals will be dosed twice daily for 3 or 5 days. Baseline measurements will be performed before the first dose ever. On the last day, animals will only get dosed once and measured before this last dose, then 15 min, 1 hr, 8 hr, and 24 hours post last dose.

Taken together, the above studies demonstrate that a TRPM8 antagonist, in particular Compound I as used above, can be used to treat or prevent ocular disorders, such as dry eye or severe dry eye.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

Each reference, patent and patent application referred to in the instant application is hereby incorporated by reference as if each reference were noted to be incorporated individually.

What is claimed is:

1. A method of alleviating at least one ocular discomfort in a subject in need thereof comprising administering to the subject a unit dose of a composition comprising 0.001-5.0% (w/v) of a transient receptor potential melastatin 8 (TRPM8) antagonist, of Compound I:

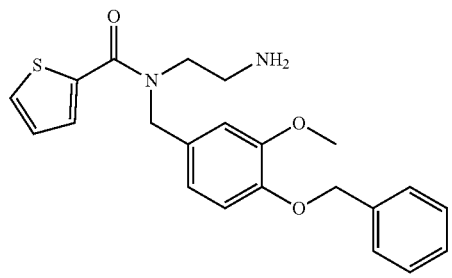 [SMILES: COc1cc(CN(CCN)C(=O)c2cccs2)ccc1OCc1ccccc1]

wherein the at least one ocular discomfort comprises ache, dryness, itchiness, a gritty sensation, redness, sensitivity to light, stinging sensation, burning sensation, or pain associated with the eye.

2. The method of claim 1, wherein the composition is administered topically to the eye.

3. The method of claim 2, wherein the eye comprises a tissue or gland in or around the eye selected from the group consisting of ocular tissue, eyelids of the subject, ocular surface, meibomian gland, lid margin and or lacrimal gland.

4. The method of claim 1, wherein the composition is in the form of a solid, a paste, an ointment, a gel, a liquid, an aerosol, a mist, a polymer, insert, implant, a film, an emulsion, or a suspension.

5. The method of claim 1, wherein TRPM8 antagonist is at a concentration of 0.1% (w/v).

6. The method of claim 1, wherein the TRPM8 antagonist is administered in combination with another agent.

* * * * *